US010905359B2

(12) United States Patent
Barretto et al.

(10) Patent No.: US 10,905,359 B2
(45) Date of Patent: Feb. 2, 2021

(54) APPARATUS, SYSTEM, METHOD, AND COMPUTER PROGRAM FOR DISTINGUISHING BETWEEN ACTIVE AND INACTIVE TIME PERIODS OF A SUBJECT

(71) Applicant: KONINKLIJKE PHILIPS N.V., Eindhoven (NL)

(72) Inventors: Chevone Marie Barretto, Cambridge (GB); Rita Priori, Cambridge (GB)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 322 days.

(21) Appl. No.: 15/735,328

(22) PCT Filed: Jun. 13, 2016

(86) PCT No.: PCT/EP2016/063448
§ 371 (c)(1),
(2) Date: Dec. 11, 2017

(87) PCT Pub. No.: WO2016/198685
PCT Pub. Date: Dec. 15, 2016

(65) Prior Publication Data
US 2018/0168486 A1  Jun. 21, 2018

(30) Foreign Application Priority Data
Jun. 12, 2015 (EP) .................................. 15171920

(51) Int. Cl.
*A61B 5/00* (2006.01)
*A61B 5/11* (2006.01)
(Continued)

(52) U.S. Cl.
CPC .......... *A61B 5/1118* (2013.01); *A61B 5/0816* (2013.01); *A61B 5/7264* (2013.01);
(Continued)

(58) Field of Classification Search
CPC ... A61B 5/1118; A61B 5/1123; A61B 5/0816; A61B 5/7264; G16H 20/30; G06F 19/3481
See application file for complete search history.

(56) References Cited

U.S. PATENT DOCUMENTS 8,758,262 B2   6/2014  Rhee et al.
8,880,377 B2*  11/2014 Niemimaki .......... G01C 22/006
                                                    702/141
(Continued)

FOREIGN PATENT DOCUMENTS

JP    2012024521 A    2/2012
JP    2012040189 A    3/2012
(Continued)

OTHER PUBLICATIONS

Sandroff, Brian M. et al., "Accelerometer cut-points derived during over-ground walking in persons with mild, moderate, and severe multiple sclerosis", Journal of Neurological Sciences, vol. 340, No. 1, Feb. 28, 2014, pp. 50-57, XP028658318, ISSN: 0022-510X.
(Continued)

*Primary Examiner* — Max F Hindenburg

(57) ABSTRACT

The present invention relates to an apparatus (100), system (200), method (300), and computer program for distinguishing between active and inactive time periods of a subject. An input unit (110) receives time-dependent activity data (120) (e.g., corresponding to a level of activity). An activity threshold providing unit (130) provides an activity threshold (140) for the subject. An activity assessment unit (150) classifies the time-dependent activity data (120) based on the activity threshold (140). The activity threshold providing unit (130) provides the activity threshold (140) individually for said subject. The present invention provides an approach to patient-tailor the activity threshold (140) for periods of activity and inactivity.

14 Claims, 3 Drawing Sheets

(51) Int. Cl.
*G06F 19/00* (2018.01)
*G16H 20/30* (2018.01)
*A61B 5/08* (2006.01)

(52) U.S. Cl.
CPC ......... *G06F 19/3481* (2013.01); *G16H 20/30* (2018.01); *A61B 5/08* (2013.01); *A61B 5/4833* (2013.01); *A61B 2505/09* (2013.01)

(56) References Cited

U.S. PATENT DOCUMENTS

| | | | |
|---|---|---|---|
| 9,474,970 B2* | 10/2016 | Kil | G06Q 10/101 |
| 9,901,815 B2* | 2/2018 | Sarrafzadeh | G06Q 50/10 |
| 10,463,278 B2* | 11/2019 | Homsi | A61B 5/6824 |
| 2004/0111041 A1 | 6/2004 | Ni et al. | |
| 2010/0069203 A1 | 3/2010 | Kawaguchi et al. | |
| 2011/0166463 A1 | 7/2011 | Xi | |
| 2012/0059664 A1 | 3/2012 | Georgiev et al. | |
| 2012/0220474 A1 | 8/2012 | Kennedy et al. | |
| 2013/0053990 A1 | 2/2013 | Ackland | |
| 2013/0237882 A1 | 9/2013 | Niemimaki | |
| 2014/0135612 A1* | 5/2014 | Yuen | A61B 5/02405 600/407 |
| 2014/0244009 A1 | 8/2014 | Mestas | |
| 2014/0279754 A1 | 9/2014 | Barsoum et al. | |

FOREIGN PATENT DOCUMENTS

| | | |
|---|---|---|
| JP | 2012235920 A | 12/2012 |
| RU | 101347 U1 | 1/2011 |
| WO | 2006009830 A2 | 1/2006 |

OTHER PUBLICATIONS

Parkka, J. et al., "Personalization Algorithm for Real-Time Activity Recognition Using PDA, Wireless Motion Bands, and Binary Decision Tree", IEEE Transactions on Information Technology in Biomedicine, IEEE Service Center, Los Alamitos, CA, US, vol. 13, No. 5, Sep. 1, 2010, pp. 1211-1215.

Perriot, B. et al., "Characterization of Physical Activity in COPD Patients: Validation of a Robust Algorithm for Actigraphic Measurements in Living Situations", IEEE Journal of Biomedical and Health Informatics, IEEE, Piscataway, NJ, USA, vol. 18, No. 4, Jul. 1, 2014, pp. 1225-1231.

Van Remoortel, H. et al., "Moderate Intense Physical Activity Depends on Selected Metabolic Equivalent of Task (Met) Cut-Off and Type of Data Analysis", PLOS One, vol. 8, No. 12, Dec. 20, 2013.

Coronado, M. et al., "Walking Activity Measured by Accelerometry During Respiratory Rehabilitation", Accelerometry During Rehabilitation, Journal of Cardiopulmonary Rehabilitation, pp. 357-264, 2003.

* cited by examiner

FIG. 4

|     | 25th | 30th | 40th | 50th | 75th | 80th | 90th | 95th |
|-----|------|------|------|------|------|------|------|------|
| P02 | 0.13 | 0.14 | 0.22 | 0.39 | 0.93 | 1.11 | 1.92 | 3.04 |
| P04 | 0.16 | 0.18 | 0.23 | 0.29 | 0.49 | 0.55 | 0.77 | 1.10 |
| P05 | 0.09 | 0.12 | 0.19 | 0.26 | 0.63 | 0.75 | 1.44 | 2.03 |
| P10 | 0.13 | 0.15 | 0.20 | 0.29 | 0.84 | 1.01 | 1.83 | 2.73 |
| P11 | 0.18 | 0.23 | 0.38 | 0.54 | 1.20 | 1.47 | 2.58 | 3.81 |
| P12 | 0.12 | 0.14 | 0.19 | 0.27 | 0.54 | 0.62 | 0.99 | 1.35 |
| P14 | 0.09 | 0.10 | 0.15 | 0.24 | 0.62 | 0.71 | 1.04 | 1.38 |

FIG. 5

| Time | | M | | Tu | | W | | Th | | F | |
|------|------|----|----|----|----|----|----|----|----|----|----|
| | | G3 | G4 | G3 | G4 | G3 | G4 | G3 | G4 | G3 | G4 |
| 7:30 | 7:45 | | | | | | | | | | |
| 7:45 | 8:00 | | | | | | | | | | |
| 8:00 | 8:15 | | | | | | | | | | |
| 8:15 | 8:30 | | | | | | | | | 530 | 560 |
| 8:30 | 8:45 | 520 | 530 | 530 | | | | | | | |
| 8:45 | 9:00 | | | | | | | | 570 | 530 | | 530 |
| 9:00 | 9:15 | | | | | | | 570 | 530 | | 530 |
| 9:15 | 9:30 | | | 530 | | 530 | | | | | |
| 9:30 | 9:45 | | 570 | | | | | | | | |
| 9:45 | 10:00 | 530 | | | | | | | | 550 | 550 |
| 10:00 | 10:15 | 530 | | | 570 | 530 | | 530 | | | |
| 10:15 | 10:30 | | | 540 | | | | | | | |
| 10:30 | 10:45 | | | | | | | | | | |
| 10:45 | 11:00 | | 540 | | | | 540 | | 540 | 540 | |
| 11:00 | 11:15 | | | | | | | | | | |
| 11:15 | 11:30 | | | | | | | | | | |
| 11:30 | 11:45 | 540 | | 580 | 540 | 540 | 560 | 540 | 570 | | 540 |
| 11:45 | 12:00 | | | | | | | | | | |
| 12:00 | 12:15 | | | | | | | | | | |
| 12:15 | 12:30 | | | | | | | | | | |
| 12:30 | 12:45 | | | | | | | | | | |
| 12:45 | 13:00 | | | | | | | | | | |
| 13:00 | 13:15 | 550 | 550 | 550 | 550 | 550 | 550 | 550 | 550 | 530 | 580 |
| 13:15 | 13:30 | | | | | | | | | | |
| 13:30 | 13:45 | | | | | | | | | | |
| 13:45 | 14:00 | | | | | | | | | | |
| 14:00 | 14:15 | | | | | | | | | | |
| 14:15 | 14:30 | | | | | | | | | | |
| 14:30 | 14:45 | | | | | | | | | | |
| 14:45 | 15:00 | | | | | | | | | | |
| 15:00 | 15:15 | | | | | | | | | | |
| 15:15 | 15:30 | 560 | 530 | 530 | 520 | 560 | 530 | 520 | 530 | 560 | 530 |
| 15:30 | 15:45 | | | | | | | | | | |
| 15:45 | 16:00 | | | | | | | | | | |
| 16:00 | 16:15 | 530 | 560 | | 530 | 530 | | 530 | 520 | | |
| 16:15 | 16:30 | | | | | | | | | | |
| 16:30 | 16:45 | | | | | | | | | | |
| 16:45 | 17:00 | | | | | | | | | | |

APPARATUS, SYSTEM, METHOD, AND COMPUTER PROGRAM FOR DISTINGUISHING BETWEEN ACTIVE AND INACTIVE TIME PERIODS OF A SUBJECT

CROSS-REFERENCE TO PRIOR APPLICATIONS

This application is the U.S. National Phase application under 35 U.S.C. § 371 of International Application Serial No. PCT/EP2016/063448, filed on 13 Jun. 2016, which claims the benefit of European Application No. 15171920.0, filed on 12 Jun. 2015. These applications are hereby incorporated by reference herein.

FIELD OF THE INVENTION

The invention relates to an apparatus, system, method, and computer program for distinguishing between active and inactive time periods of a subject.

BACKGROUND OF THE INVENTION

Chronic obstructive pulmonary disease (COPD) refers broadly to a group of conditions that cause irreversible respiratory impairment by increasing obstruction to airflow through the bronchi of the lungs. To improve the quality of COPD patient's lives and reduce healthcare costs, there is a need to support COPD patients from the hospital to the home.

Compared with age-matched control subjects, studies have shown that clinically stable COPD patients are significantly physically less active and are limited in their physical activity due to their condition. Physical activity monitors are frequently used to estimate levels of daily physical activity. These devices usually measure the body's acceleration on one, two or three axes and translate it into an estimate of active energy expenditure. Specifically, the activity monitor's output provides information on the activity-related energy expenditure. This output is in turn representative of the amount of movement or physical activity performed by the subject wearing the activity monitor. Activity devices typically convert measured acceleration into some kind of output, such as, e.g., activity counts or calories.

Unfortunately there is no unique measurement unit which is used to quantify physical activity by means of activity monitors, but rather each device measures physical activity based on a variety of algorithms and each device outputs the measurement in an arbitrary unit that can be for example Metabolic Equivalent of Tasks (METs) or activity counts or vector magnitude units (reflecting acceleration).

The article "*Walking Activity Measured by Accelerometry During Respiratory Rehabilitation*" by M. Coronado et al, Journal of Cardiopulmonary Rehabilitation, volume 23, pages 357 to 364 (2003), discloses individually calibrating the accelerometer at different walking speeds, and subsequently recording whole-day physical activity for fifteen patients with chronic obstructive pulmonary disease on the first and the last days of the program, and for ten healthy subjects. Data are expressed as percentage of time spent in inactivity, low level activity, and medium level activity, with the latter corresponding to usual walking speed.

SUMMARY OF THE INVENTION

It is an object of the present invention to provide an improved apparatus for distinguishing between active and inactive time periods of a subject, an improved system for distinguishing between active and inactive time periods of a subject, an improved method for distinguishing between active and inactive time periods of a subject, and an improved computer program for distinguishing between active and inactive time periods of a subject.

In an aspect of the invention, there is provided an apparatus for distinguishing between active and inactive time periods of a subject. The apparatus comprises an input unit for receiving time-dependent activity data for said subject, wherein said time-dependent activity data is characterized by a level of activity of said subject during a first time period; an activity threshold providing unit that is configured to provide an activity threshold for said subject; and an activity assessment unit that is configured to classify said time-dependent activity data based on said activity threshold. Said activity threshold providing unit is configured to provide said activity threshold individually for said subject. Said apparatus further comprises an activity threshold calibration unit that is configured to calibrate said activity threshold providing unit based on a comparison of said level of activity to an expected level of activity.

The present invention provides an approach to patient tailor a threshold for periods of activity and inactivity, which are compatible with typical guidelines for COPD patients (and can be applied to other groups of patients that have limited exercise capacity). The threshold may thus serve to distinguish physical activity at different intensity levels. It is noted however that the concept of distinguishing active from inactive periods may also be applied to subjects not suffering from COPD, or to subjects not having a limited exercise capacity. In general, different types of activities can be classified as a moderate intensity level (e.g. housework) or a vigorous intensity level (e.g. running). In an embodiment, a range of values are set as a temporary threshold and the number of bouts above each respective threshold is measured based on the data from an activity monitor. The term "bout" typically refers to a period of time during which something is done or happening. Many embodiments herein refer to "10 minute bouts", but the actual time period (i.e., ten minutes, twenty minutes, etc.) can be chosen based on e.g. the subject's schedule. For instance, if 30 minutes of treadmill exercise are scheduled, one would expect three "active" 10-minute bouts of activity. If 60 minutes of walking are scheduled, one would expect six "active" 10-minute bouts of activity. Thresholds are calibrated using the known bouts (based on the schedules of the patient) and the measured bouts to get a final threshold that is individual to a patient. The present invention therefore can be applied to various types of activities.

An expected level of activity may correspond to a known level of activity. In an embodiment, the comparison is based on the relation between the measured bouts of activity (as obtained, e.g., from an activity monitor) above said activity threshold versus the known "active" bouts based, e.g., on the subject's schedule of activity. The concept of Metabolic Equivalents of Task (METs) is commonly used to set thresholds and guidelines to the general population, where light, moderate and vigorous intensity activities can be categorized by the energy expenditure in metabolic equivalent of tasks. For example, any activity that is in the range of 3 to 6 METs is considered as "moderate" while any activity above 6 METs is considered as vigorous. It is noted that MET estimates typically apply to healthy adults. Moderate-intensity activities are typically defined as those that get the subject moving fast enough or strenuously enough to burn off three to six times as much energy per minute as when sitting quietly, or exercises that clock in at 3 to 6 METs. Vigorous-intensity activities burn more than 6 METs. For example, walking at 4.5 to 6.5 km/h is considered to require 4 METs and to be a moderate-intensity activity, regardless of who is doing the activity. This might be easy for a fit adult, but harder for an older person.

As noted above, the activity threshold providing unit is configured to provide said activity threshold individually for the subject. In other words, the present invention eliminates the need for predetermined thresholds that can be applied to the acceleration data, but provides "patient-tailored" thresholds. Of course, this does not mean that the activity thresholds for two different patients are necessarily different as well. Rather, the present invention proposes to assess a subject's activity and energy expenditure to evaluate a subject-appropriate activity threshold so as to be able to automatically decide whether the subject is active or inactive. Additionally and/or alternatively, the present invention proposes to assess a subject's activity and energy expenditure to evaluate a subject-appropriate activity threshold so as to be able to automatically decide whether the subject is performing an activity at a certain intensity level, such as, e.g. moderate or vigorous.

In an embodiment, said apparatus further comprises an activity identification unit that is configured to identify a type of activity of said subject. By identifying the type of activity (such as, e.g., body awareness, treadmill exercise, strength exercise, walking, arm exercise, etc.), calibration is further facilitated in that the apparatus can make use of typical activity levels for known activities. In an embodiment, a "known" activity may correspond to an activity, where the activity type is known because of, e.g., the subject's schedule. In a further embodiment, said apparatus further comprises an activity identification unit that is configured to identify a type of activity of said subject; wherein said type of activity is provided to said activity threshold providing unit, wherein said activity threshold is provided based on said type of activity.

In a further embodiment, said apparatus further comprises an activity threshold calibration unit that is configured to calibrate said activity threshold providing unit based on a comparison of said level of activity to an expected level of activity; wherein said activity threshold calibration unit comprises a regression analysis unit that is configured to perform a regression analysis between said level of activity and said expected level of activity. In an example, this corresponds to performing a linear regression between said level of activity and said expected level of activity.

In a further embodiment, said apparatus further comprises an activity threshold calibration unit that is configured to calibrate said activity threshold providing unit based on a comparison of said level of activity to an expected level of activity; wherein said activity threshold calibration unit comprises a receiver operating characteristic unit. For instance, the receiver operating characteristic unit may be configured to illustrate the performance of a binary classifier system as its discrimination threshold is varied. The receiver operating characteristic curve is a tool for evaluating the performance of the threshold. The sensitivity, specificity, positive and negative predictive value are determined for each temporary threshold. Each bout of data will be defined as active or inactive. The receiver operating characteristic curve will then evaluate the performance of each temporary threshold in classifying whether each bout is active or inactive.

In a further embodiment, said apparatus further comprises an activity threshold calibration unit that is configured to calibrate said activity threshold providing unit based on a comparison of said level of activity to an expected level of activity, wherein said activity threshold calibration unit comprises a regression analysis unit that is configured to perform a regression analysis between said level of activity and said expected level of activity; wherein said regression analysis provides a plurality of regression parameters, and said activity threshold is provided based on said plurality of regression parameters.

In a further embodiment, said apparatus further comprises an activity threshold calibration unit that is configured to calibrate said activity threshold providing unit based on a comparison of said level of activity to an expected level of activity, wherein said activity threshold calibration unit comprises a regression analysis unit that is configured to perform a regression analysis between said level of activity and said expected level of activity; wherein said regression analysis provides a plurality of regression parameters, and said activity threshold is provided based on said plurality of regression parameters; wherein said activity threshold is provided by minimizing an error associated with said regression analysis. Said error may correspond to the sum of the squares of the offset of the data points from the estimated curve.

In a further embodiment, said apparatus further comprises an activity identification unit that is configured to identify a type of activity of said subject based on a range and mean energy expenditure of said subject. For example, based on the schedule and activity data, one might find that a bout of activity with a value between 100 to 150 activity counts has an 80% chance of it being categorized as jogging. In that same example, the activity "jogging" would consequently have a mean activity count of 125.

In a further embodiment, said activity threshold corresponds to said subject's mean energy expenditure for a time period during which said subject is performing a baseline activity. In an embodiment, said baseline activity corresponds to at least one from the group of walking, jogging, stretching, swimming, running, yoga, etc. Choosing the mean energy expenditure during a baseline activity (such as, e.g., walking) serves as a natural delimitation between moderate and vigorous activity. As noted above, other activities that may serve to determine an activity threshold might be jogging, stretching, swimming, running, yoga, etc.

In a further embodiment, said apparatus further comprises an activity threshold calibration unit that is configured to calibrate said activity threshold providing unit based on a comparison of said level of activity to an expected level of activity, wherein said expected level of activity is determined based on the subject's schedule. The subject's schedule may correspond to a known plan of activities for a given time period. For instance, the subject's schedule may comprise the information that the subject is running from 9 am to 10 am and swimming from 1 pm to 1:30 pm. From this, an expected level of activity may be derived. The following table shows the mean values and standard deviation for some activities based on the schedule and activity data.

| Energy expenditure (Active Energy Expenditure (AEE) per Basal Weight (BW) | | |
|---|---|---|
| Pulmonary rehab | Mean value | Standard deviation |
| Outdoor walking | 1.01 | 0.32 |
| Treadmill | 0.81 | 0.33 |

-continued

Energy expenditure (Active Energy Expenditure (AEE) per Basal Weight (BW))

| Pulmonary rehab | Mean value | Standard deviation |
| --- | --- | --- |
| Strength exercise | 0.50 | 0.16 |
| Arm exercise | 0.63 | 0.50 |

In a further embodiment, said time-dependent activity data corresponds to activity data as a function of time gathered during a first time period.

In another aspect of the invention, there is provided a system for distinguishing between active and inactive time periods of a subject, the system comprising: a physical activity measurement unit that is configured to gather time-dependent activity data for said subject; and the apparatus; wherein said input unit of said apparatus is configured to receive said time-dependent activity data from said physical activity measurement unit.

In an embodiment, said system comprises a storage unit configured to store said time-dependent activity data. By providing a storage unit, time-dependent activity data may be stored for later analysis and re-processing. It is further conceivable to transfer the activity data directly to a personal trainer, nurse, and/or physician who may then assess the calibration.

In another aspect of the invention, there is provided a method for distinguishing between active and inactive time periods of a subject; said method comprising the steps of receiving time-dependent activity data for said subject, wherein said time-dependent activity data is characterized by a level of activity of said subject during a first time period; providing an activity threshold for said subject; and classifying said time-dependent activity data based on said activity threshold. Said activity threshold is provided individually for said subject. Said activity threshold is calibrated based on a comparison of said level of activity to an expected level of activity.

In another aspect of the invention, there is provided a computer program for distinguishing between active and inactive time periods of a subject, the computer program comprising program code means for causing the apparatus for distinguishing between active and inactive time periods of a subject to carry out the steps of the method for distinguishing between active and inactive time periods of a subject, when the computer program is run on a computer controlling the apparatus for distinguishing between active and inactive time periods of a subject.

It shall be understood that the apparatus for distinguishing between active and inactive time periods of a subject of claim 1, the system for distinguishing between active and inactive time periods of a subject of claim 11, the method for distinguishing between active and inactive time periods of a subject of claim 13, and the computer program for distinguishing between active and inactive time periods of a subject of claim 14 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

BRIEF DESCRIPTION OF THE DRAWINGS

In the following drawings:

FIG. 4 shows a table with some examples of the 25th, 30th, 40th, 50th, 75th, 80th, 90th and 95th percentiles of physical activity in METs over one day for a 10 minute intervals for different subjects, FIG. 5 shows an example of a schedule during pulmonary rehab along with the known number of 'active' 10 minute bouts where activities are scheduled for different periods of the day.

DETAILED DESCRIPTION OF EMBODIMENTS

Figure 1:
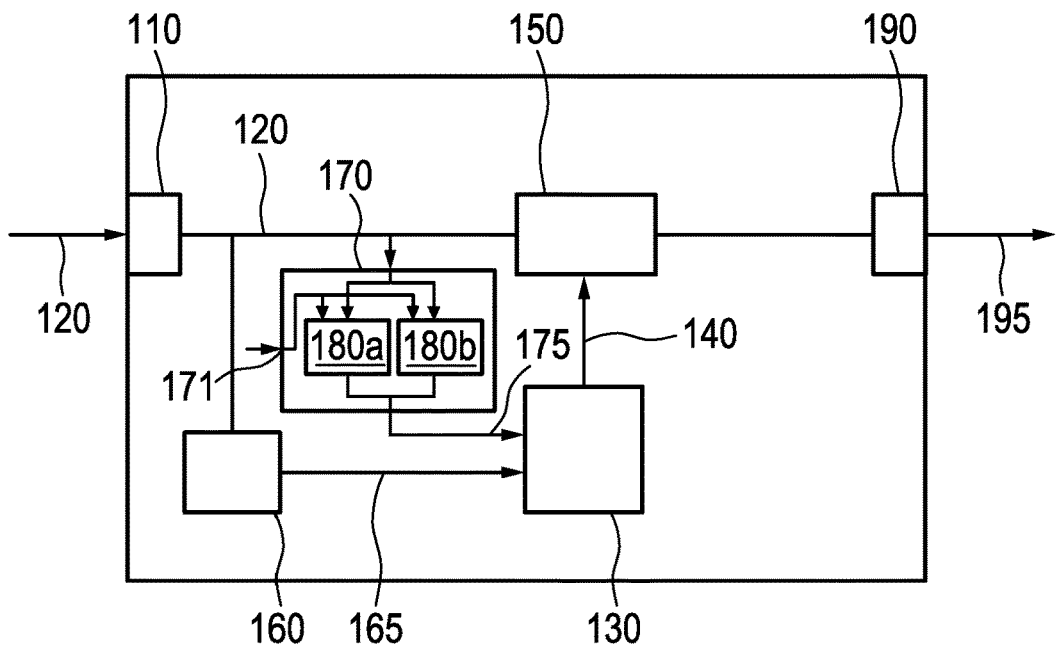
FIG. 1 shows schematically and exemplary an embodiment of an apparatus for distinguishing between active and inactive time periods of a subject.

A recommended minimum amount of physical activity is 30 minutes of moderately intense aerobic physical activity at least five days a week or 20 minutes of vigorously intense aerobic physical activity at least three days a week. Physical activity is an important tool in managing chronic obstructive pulmonary disease (COPD). To estimate levels of daily physical activity, physical activity monitors are frequently used, but unfortunately there is no unique measurement unit which can be used to quantify if the intensity and duration of physical activity is in line with the guidelines, when these activity monitors are used. Moreover, detecting moderate to vigorous physical activity becomes very challenging in COPD patients due to the general lower level of activity. Moreover, what is categorized as moderate to vigorous intensity in COPD patients may not necessarily be the same for a healthy subject. Therefore, a tailored approach is needed.

The present invention relates to a patient tailored approach to determine periods and intensities of activity and inactivity in patients with chronic diseases that are compatible with the guidelines on physical activity independently of the device that is used.

Chronic obstructive pulmonary disease (COPD) is a progressive and irreversible disease which is under-diagnosed, life-threatening and mainly interferes with normal breathing. Individuals who suffer from COPD experience an intense shortness of breath during exercise, which causes a general disability. Daily activities, such as walking, can become very difficult due to breathlessness as the condition gradually worsens.

Physical activity is an important tool in managing COPD. An active lifestyle and regular physical activity has shown to be positively associated with outcomes such as exercise capacity and health-related quality of life. Studies have also shown that clinically stable COPD are physically inactive when compared with age-matched control subjects and are limited in their physical activity due to their condition.

The Metabolic Equivalent of Task (MET) is a physiological measure expressing the intensity of physical activities. The concept of METs is commonly used to set thresholds and guidelines to the general population, where light, moderate and vigorous intensity activities can be categorized by the energy expenditure in metabolic equivalent of tasks (MET). For example any activity that is in the range of 3 to 6 METs is considered as moderate while any activity corresponding to more than 6 METs is considered as vigorous.

Physical activity measurement units, such as, e.g., physical activity monitors, are frequently used to estimate levels of daily physical activity. These devices may e.g. measure the body's acceleration on one, two or three axes (uniaxial, biaxial or triaxial activity monitors) and translate the determined acceleration into an estimate of energy expenditure. Unfortunately there is no unique measurement unit which is used to quantify physical activity by means of activity monitors, but rather each device measures physical activity based on a variety of algorithms and each device outputs the measurement in an arbitrary unit that can be for example METs or activity counts or vector magnitude units (reflecting acceleration). Unless each device is calibrated by measuring the average metabolic rate with a gold standard method (for example the doubly labeled water method), a process which is impractical since it needs to be performed in a lab, it is not possible to know the level of intensity of the physical activity performed by use of these arbitrary units.

Although a given list of activity may be classified under the moderate-intensity or vigorous-intensity categories (for example housework and walking domestic animals are moderate-intensity physical activities, while running and climbing up a hill are vigorous-intensity physical activity), conventional physical activity measurement units cannot easily detect the type of activity performed. It is therefore not possible to assess the actual METs, or to approximately associate a physical activity level as the type of activity is not known.

Moreover, it may be unsuitable to use these thresholds and guidelines categorizing the intensity of physical activity to determine periods of activity in COPD patients, due to their lower exercise capacity. A patient tailored threshold would be more appropriate for those patients with a limited exercise capacity.

This invention describes a patient tailored approach to determine periods of activity and inactivity in patients with chronic diseases, specifically for patients with COPD that are compatible with the guidelines on physical activity independently of the device that is used.

FIG. 1 shows schematically and exemplary an embodiment of an apparatus 100 for distinguishing between active and inactive time periods of a subject. Apparatus 100 comprises an input unit 110 for receiving time-dependent activity data 120 for said subject. Time-dependent activity data 120 is characterized by a level of activity of said subject during a first time period. An activity threshold providing unit 130 is configured to provide an activity threshold 140 for said subject. An activity assessment unit 150 is configured to classify said time-dependent activity data 120 based on said activity threshold 140. Activity threshold providing unit 130 is configured to provide said activity threshold 140 individually for said subject.

Apparatus 100 further comprises an activity identification unit 160 that is configured to identify a type of activity 165 of said subject. In the embodiment of FIG. 1, type of activity 165 is provided to said activity threshold providing unit 130, so that activity threshold 140 may be provided based on type of activity 165.

Apparatus 100 further comprises an activity threshold calibration unit 170 that is configured to calibrate said activity threshold providing unit 130 based on a comparison of said level of activity to an expected level of activity 171. In the embodiment of FIG. 1, activity threshold calibration unit 170 comprises an optional regression analysis unit 180a that is configured to perform a regression analysis between said level of activity and expected level of activity 171. Regression analysis unit 180a is configured to provide a plurality of regression parameters, and said activity threshold 140 is provided based on said plurality of regression parameters. Specifically, activity threshold 140 may be provided by minimizing an error associated with said regression analysis. Activity threshold calibration unit 170 may additionally and/or alternatively comprise optional receiver operating characteristic unit 180b. Optional receiver operating characteristic unit 180b may be configured to illustrate the performance of a binary classifier system as its discrimination threshold is varied. A receiver operating characteristic (ROC) curve evaluates the performance of different thresholds when detecting active bouts. Based on this evaluation, sensitivity, specificity, positive predictive value (PPV), negative predictive value (NPV), etc. may be calculated for each threshold. The receiver operating characteristic curve is a tool for evaluating the performance of the threshold. The sensitivity, specificity, positive and negative predictive value are determined for each temporary threshold. Each bout of data will be defined as active or inactive. The receiver operating characteristic curve will then evaluate the performance of each temporary threshold in classifying whether each bout is active or inactive.

Activity identification unit 160 may be configured to identify said type of activity based on a range and mean energy expenditure of said subject. Activity threshold 140 may correspond to said subject's mean energy expenditure for a time period during which said subject is walking. As illustrated in further detail below, said expected level of activity is determined based on the subject's schedule. Time-dependent activity data 120 corresponds to activity data as a function of time gathered during a first time period.

Figure 2:
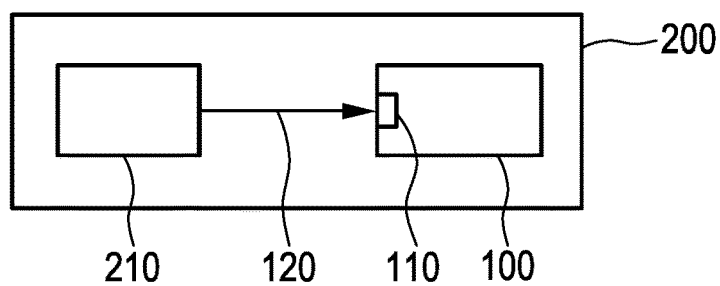
FIG. 2 shows schematically and exemplary an embodiment of a system for distinguishing between active and inactive time periods of a subject.

FIG. 2 shows schematically and exemplary an embodiment of a system 200 for distinguishing between active and inactive time periods of a subject. System 200 comprises a physical activity measurement unit 210 that is configured to gather time-dependent activity data 120 for said subject; and apparatus 100. Input unit 110 of apparatus 100 is configured to receive time-dependent activity data 120 from physical activity measurement unit 210. System 200 may further comprise a storage unit (not shown) configured to store time-dependent activity data 120.

Figure 3:
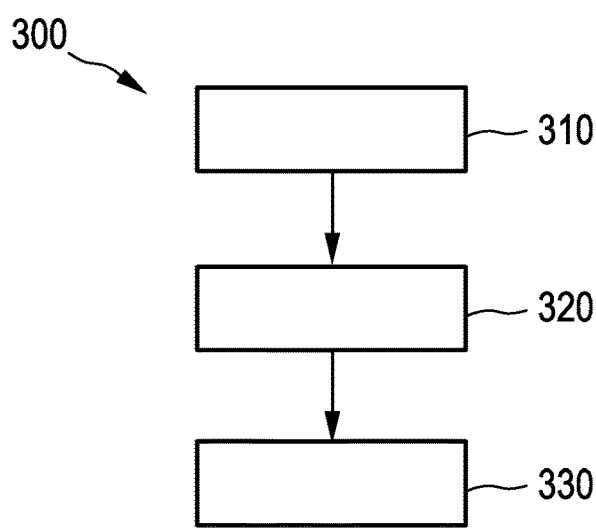
FIG. 3 shows schematically and exemplary an embodiment of a method for distinguishing between active and inactive time periods of a subject.

FIG. 3 shows schematically and exemplary an embodiment of a method 300 for distinguishing between active and inactive time periods of a subject. In a step 310, the method comprises receiving time-dependent activity data 120 for said subject, wherein said time-dependent activity data 120 is characterized by a level of activity of said subject during a first time period. In a step 320, the method comprises providing an activity threshold 140 for said subject. In a step 330, the method comprises classifying said time-dependent activity data 120 based on said activity threshold 140. Activity threshold 140 is provided individually for said subject.

During pulmonary rehab, patients follow a specific schedule of activities that fall into the moderate-intensity and vigorous-intensity physical activity categories and continuously wear a physical activity measurement unit, such as e.g. an activity monitor, throughout the period. The physical activity measurement unit will output minute by minute data reflecting the energy expenditure, for example in activity counts, calories, or METs.

In an embodiment, a patient-tailored threshold for identifying an 'Active' period is provided based on the distribution of activity data. The distribution of activity data during pulmonary rehab may be used as follows:

For each patient, compute the distribution of the activity levels quantified in an arbitrary unit given by the activity monitor during pulmonary rehab for an interval of 'x' minutes, in the following examples a 10 minute interval has been used.

The table in FIG. 4 shows some examples of the $25^{th}$, $30^{th}$, $40^{th}$, $50^{th}$, 75th, 80th, $90^{th}$ and $95^{th}$ percentiles of physical activity in METs over one day for a 10 minute intervals for different subjects. The distribution of a subject's mean MET values of the entire time in rehab is shown. By considering percentiles, initial temporary thresholds may be set for further testing. For patient P02, the $50^{th}$ percentile corresponds to a median MET value of 0.39. In other words, during half of the 10 minute intervals during rehab, patient P02 exhibited a median MET value below 0.39.

In pulmonary rehab, each patient performs a set amount of activities, therefore the number of 10 minute bouts spent in scheduled moderate- and vigorous-intensity activities is known.

FIG. 5 shows an example of a week schedule during pulmonary rehab along with the known number of 'active' 10 minute bouts where activities (e.g., body awareness 520, treadmill 530, strength exercise 540, walking 550, arm exercises 560, sports 570, relaxation 580) of two groups G3 and G4 are scheduled for different periods (e.g., 8:30-8:45, 8:45-9:00, etc.) of the day (Monday M, Tuesday Tu, Wednesday W, Thursday Th, Friday F). In the example shown in FIG. 5, the number of 10-minute bouts spent in scheduled moderate- and vigorous-intensity activities corresponds to ca. 12 bouts in the morning and ca. 5 to 8 bouts in the afternoon. Considering the day-to-day variations, the number of 10-minute bouts spent in scheduled moderate- and vigorous-intensity activities corresponds to ca. 20 bouts on Monday, Wednesday, Thursday, and Friday, and to ca. 17 bouts on Tuesday. In particular, the number of bouts can be deduced from the type and length of activities. For instance, if 30 minutes of treadmill exercise are scheduled, one would expect three "active" 10-minute bouts of activity. If 60 minutes of walking are scheduled, one would expect six "active" 10-minute bouts of activity.

An 'active' threshold tailored to a patient is a number above which the activity being measured can be considered as at least at a moderate-intensity level. To compute the tailored threshold, the known number of bouts of 10-minute activities is compared to the number of measured bouts of 10-minute activities by iteratively setting each percentile as a temporary threshold and performing the following steps. It shall be understood however that the present embodiment is of course not limited to 10-minute-intervals, but other time periods are conceivable as well.

First, for each temporary threshold compute the average number of bouts above the threshold over the monitoring period. Second, compare the number of bouts above the temporary threshold with the known number of active bouts. Third, perform a regression analysis between the known number of active bouts and the measured number of active bouts, and calculate the regression parameters.

Additionally, the percentage error between the known number of active bouts and the measured number of active bouts may be calculated.

Ideally an optimum threshold corresponds to a slope of 1 and an error equal to zero. The thresholds corresponding to the distinguishing threshold between 'active' and 'inactive', i.e., the 'active' threshold may be chosen as the percentile that gives the slope closest to 1 and that gives the lowest error.

Figure 6:
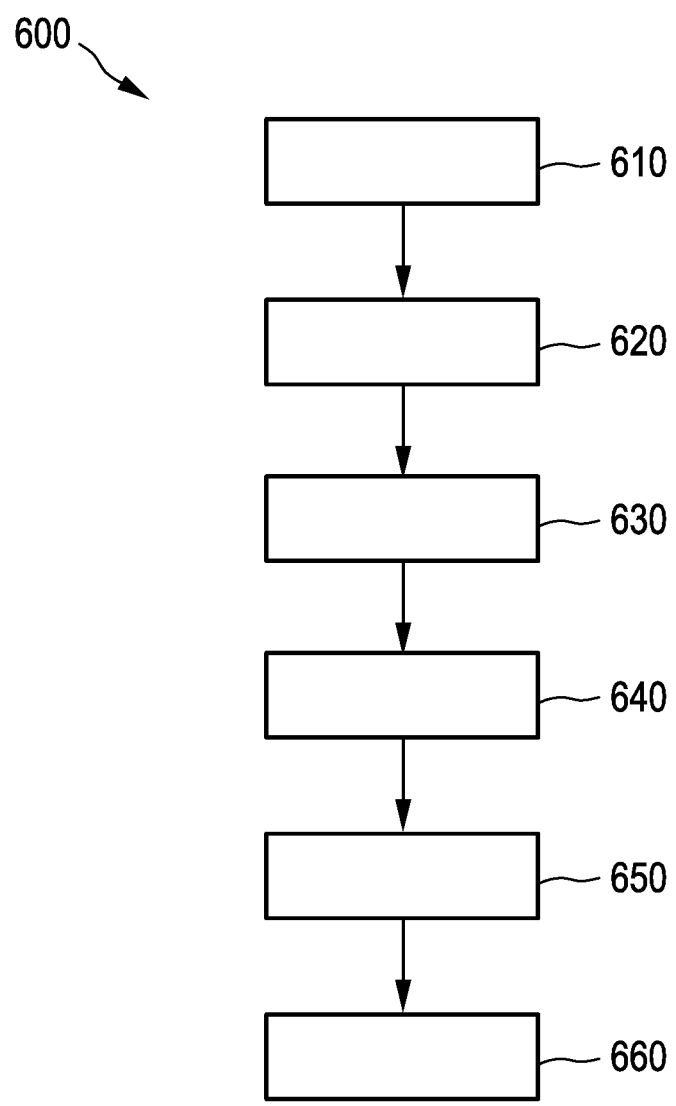
FIG. 6 shows schematically and exemplary an embodiment of a method for distinguishing between active and inactive time periods of a subject.

The procedure 600 is further illustrated in FIG. 6. In a step 610, an agenda of activities (such as, e.g., the weekly schedule shown in FIG. 5) is provided. In a step 620, the patient is asked to wear a physical activity measurement unit preferably continuously throughout a monitoring period. In a step 630, bouts of 'x' minutes are identified, the distribution of activity data is determined, and respective percentiles are computed. In a step 640, each percentile is set as a threshold and the number of 'x' minute bouts above threshold is computed. For instance, one may start with the highest percentile and proceed to the lower percentiles. One may also start with the lowest percentiles and proceed to the higher percentiles. In a step 650, the percentile thresholds are calibrated by comparing known (because the weekly schedule is known) or expected 'active' bouts to measured 'active' bouts. A regression analysis may be performed aiming at an ideal slope of 1 and at a minimum error. In a step 660, a tailored threshold for an 'active' period is thus obtained.

In a further embodiment, tailored thresholds may be determined for specific moderate/high intensity activities. Based on the patient's schedule, an activity of moderate/high intensity is chosen, such as e.g. running. For bouts of 'x' minutes, the range and mean energy expenditure for this activity are computed for each subject. Activities falling between the specified range may then be categorized as this type of activity (here: running).

In a further embodiment, walking is used to determine a suitable baseline. To this extent, from the agenda, periods are identified in which walking takes place. In the example of FIG. 5, subjects are walking during the time period between 13:00 and 13:30 on Monday, Tuesday, Wednesday, and Thursday. Next, the mean energy expenditure for each patient is computed. The mean energy expenditure may then be set as a patient tailored threshold for walking.

Herein, a system is disclosed that will determine periods of activity and inactivity that are in line with the guidelines on physical activity irrespectively of the activity monitor and the output measurement. In order to separate the 'active' and 'inactive' periods, an algorithm may be used which can detect the physical activity intensity and associate to a specific type of activity at a specific level of intensity.

The present invention can be used to assess the physical activity performance based on the global recommendations on physical activity for healthy life. A system is described that will determine periods of activity and inactivity for those with a lower exercise capacity than the general population, specifically targeting patients with chronic diseases.

The present invention can be used as part of a coaching scheme to determine and improve activity levels as well as encourage subjects to be more active. It is specifically designed for use in COPD, but it can also be used for other chronic diseases where staying active is important.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems. The term "computer program" may also refer to embedded software.

Any reference signs in the claims should not be construed as limiting the scope.

The present invention relates to an apparatus, system, method, and computer program for distinguishing between active and inactive time periods of a subject. An input unit receives time-dependent activity data (e.g., corresponding to a level of activity). An activity threshold providing unit provides an activity threshold for the subject. An activity assessment unit classifies the time-dependent activity data based on the activity threshold. The activity threshold providing unit provides the activity threshold individually for said subject. The present invention provides an approach to patient-tailor the activity threshold for periods of activity and inactivity.

The invention claimed is:

1. An apparatus for classifying activity of a subject, said apparatus comprising:
   an input unit for receiving time-dependent activity data for said subject, wherein said time-dependent activity data is characterized by a level of activity of said subject during a first time period;
   an activity threshold providing unit that is configured to provide an activity threshold for said subject; and
   an activity assessment unit that is configured to classify said time-dependent activity data as being either an active time period or an inactive time period based on said activity threshold;
   wherein said activity threshold providing unit is configured to provide said activity threshold individually for said subject,
   wherein said apparatus further comprises an activity threshold calibration unit that is configured to calibrate said activity threshold providing unit based on a comparison of said level of activity to an expected level of activity.

2. The apparatus as defined in claim 1,
   wherein said apparatus further comprises an activity identification unit that is configured to identify a type of activity associated with said time-dependent activity data.

3. The apparatus as defined in claim 2,
   wherein said type of activity is provided to said activity threshold providing unit wherein said activity threshold is provided based on said type of activity.

4. The apparatus as defined in claim 1,
   wherein said activity threshold calibration unit comprises a regression analysis unit that is configured to perform a regression analysis between said level of activity and said expected level of activity.

5. The apparatus as defined in claim 4,
   wherein said regression analysis unit is configured to provide a plurality of regression parameters, and said activity threshold is provided based on said plurality of regression parameters.

6. The apparatus as defined in claim 1,
   wherein said activity threshold calibration unit comprises a receiver operating characteristic unit configured for evaluating at least one of a sensitivity, a specificity, and a predictive value said activity threshold.

7. The apparatus as defined in claim 2,
   wherein said activity identification unit is configured to identify said type of activity based on a range and mean energy expenditure of said subject.

8. The apparatus as defined in claim 1,
   wherein said activity threshold corresponds to said subject's mean energy expenditure for a time period during which said subject is performing a baseline activity.

9. The apparatus as defined in claim 1,
   wherein said expected level of activity is determined based on the subject's schedule.

10. The apparatus as defined in claim 1,
    wherein said time-dependent activity data corresponds to activity data as a function of time gathered during said first time period.

11. A system for distinguishing between active and inactive time periods of a subject, the system comprising:
    a physical activity measurement unit that is configured to gather time-dependent activity data for said subject; and
    an apparatus as defined in claim 1;
    wherein said input unit of said apparatus is configured to receive said time-dependent activity data from said physical activity measurement unit.

12. The system as defined in claim 11, wherein said system comprises a storage unit configured to store said time-dependent activity data.

13. A method for classifying activity of a subject; said method comprising the steps of:
    receiving time-dependent activity data for said subject, wherein said time-dependent activity data is characterized by a level of activity of said subject during a first time period;
    providing an activity threshold for said subject; and
    classifying said time-dependent activity data as being either an active time period or an inactive time period based on said activity threshold;
    wherein said activity threshold is provided individually for said subject;
    wherein said activity threshold is calibrated based on a comparison of said level of activity to an expected level of activity.

14. A computer program for classifying activity of a subject, the computer program comprising program code means for causing an apparatus to carry out the steps of the method of claim 13.

* * * * *